US 6,689,152 B2

(12) United States Patent
Balceta et al.

(10) Patent No.: US 6,689,152 B2
(45) Date of Patent: *Feb. 10, 2004

(54) INTRODUCER/DILATOR WITH BALLOON PROTECTION AND METHODS OF USE

(75) Inventors: Jobert P Balceta, San Jose, CA (US); Lorraine Mangosong, Palo Alto, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/340,180

(22) Filed: Jan. 10, 2003

(65) Prior Publication Data

US 2003/0105485 A1 Jun. 5, 2003

Related U.S. Application Data

(63) Continuation of application No. 09/547,953, filed on Apr. 12, 2000, now Pat. No. 6,569,182, which is a continuation of application No. 09/149,981, filed on Sep. 9, 1998, now Pat. No. 6,093,173.

(51) Int. Cl.[7] .............................................. A61M 29/00
(52) U.S. Cl. ............. 606/200; 604/164.08; 604/164.01; 604/170.2
(58) Field of Search ................ 604/4, 27, 28, 604/48, 500, 506–510, 96.01, 103.03, 103.05, 104, 264, 265, 171, 172, 523, 528, 164.01, 164.03, 164.08, 170.01, 170.02, 162; 600/433–435, 585; 606/200

(56) References Cited

U.S. PATENT DOCUMENTS

| 4,323,071 A | 4/1982 | Simpson et al. ............... 604/28 |
| 4,456,011 A | 6/1984 | Warnecke ..................... 606/195 |
| 4,995,872 A | 2/1991 | Ferrara ........................ 604/280 |
| 5,053,007 A | 10/1991 | Euteneuer |
| 5,053,008 A | 10/1991 | Bajaj |
| 5,108,419 A | 4/1992 | Reger et al. ................. 606/159 |
| 5,147,317 A | 9/1992 | Shank et al. ............ 604/164.13 |
| 5,151,105 A | 9/1992 | Kwan-Gett ............. 604/103.05 |
| 5,190,529 A | 3/1993 | McCrory et al. ............ 604/264 |
| 5,242,399 A | 9/1993 | Lau et al. .................... 604/104 |
| 5,330,446 A | 7/1994 | Weldon et al. |
| 5,531,715 A | 7/1996 | Engelson et al. ............ 604/265 |
| 5,549,551 A | 8/1996 | Peacock et al. ......... 604/103.05 |
| 5,702,410 A | 12/1997 | Klunder et al. |
| 5,702,417 A | 12/1997 | Hermann |
| 5,769,816 A | 6/1998 | Barbut et al. |
| 5,814,064 A | 9/1998 | Daniel et al. ................ 606/159 |
| 5,843,027 A | 12/1998 | Stone et al. |
| 5,846,260 A | 12/1998 | Maahs |
| 5,849,248 A | 12/1998 | Homberg |
| 5,891,159 A | 4/1999 | Sherman et al. ............. 606/144 |
| 5,897,567 A | 4/1999 | Ressemann et al. |
| 5,916,193 A | 6/1999 | Stevens et al. .............. 604/509 |
| 5,980,503 A | 11/1999 | Chin .......................... 604/509 |
| 6,048,331 A | 4/2000 | Tsugita et al. .......... 604/102.03 |
| 6,068,621 A | 5/2000 | Balceta et al. |
| 6,090,097 A | 7/2000 | Barbut et al. ................ 604/506 |
| 6,093,173 A | 7/2000 | Balceta et al. |
| 6,129,713 A | 10/2000 | Mangosong et al. ......... 604/264 |
| 6,231,544 B1 | 5/2001 | Tsugita et al. ............... 604/104 |
| 6,251,119 B1 | 6/2001 | Addis .......................... 128/898 |
| 6,290,710 B1 | 9/2001 | Cryer et al. ................. 606/159 |
| 6,391,044 B1 | 5/2002 | Yadav et al. ................. 606/200 |

*Primary Examiner*—Brian L. Casler
*Assistant Examiner*—Jeremy Thissell
(74) *Attorney, Agent, or Firm*—O'Melveny & Myers LLP; John Christopher James

(57) ABSTRACT

An introducer system having an elongate shaft with proximal and distal ends. A flexible sleeve is mounted on the distal end of the shaft and is adapted to circumferentially cover the outer surface of a distal end of a cannula when the shaft is positioned within a lumen of the cannula. The introducer system has dilation capabilities which facilitates insertion of a medical device into a vessel or organ. Methods of using the devices herein are also disclosed.

19 Claims, 6 Drawing Sheets

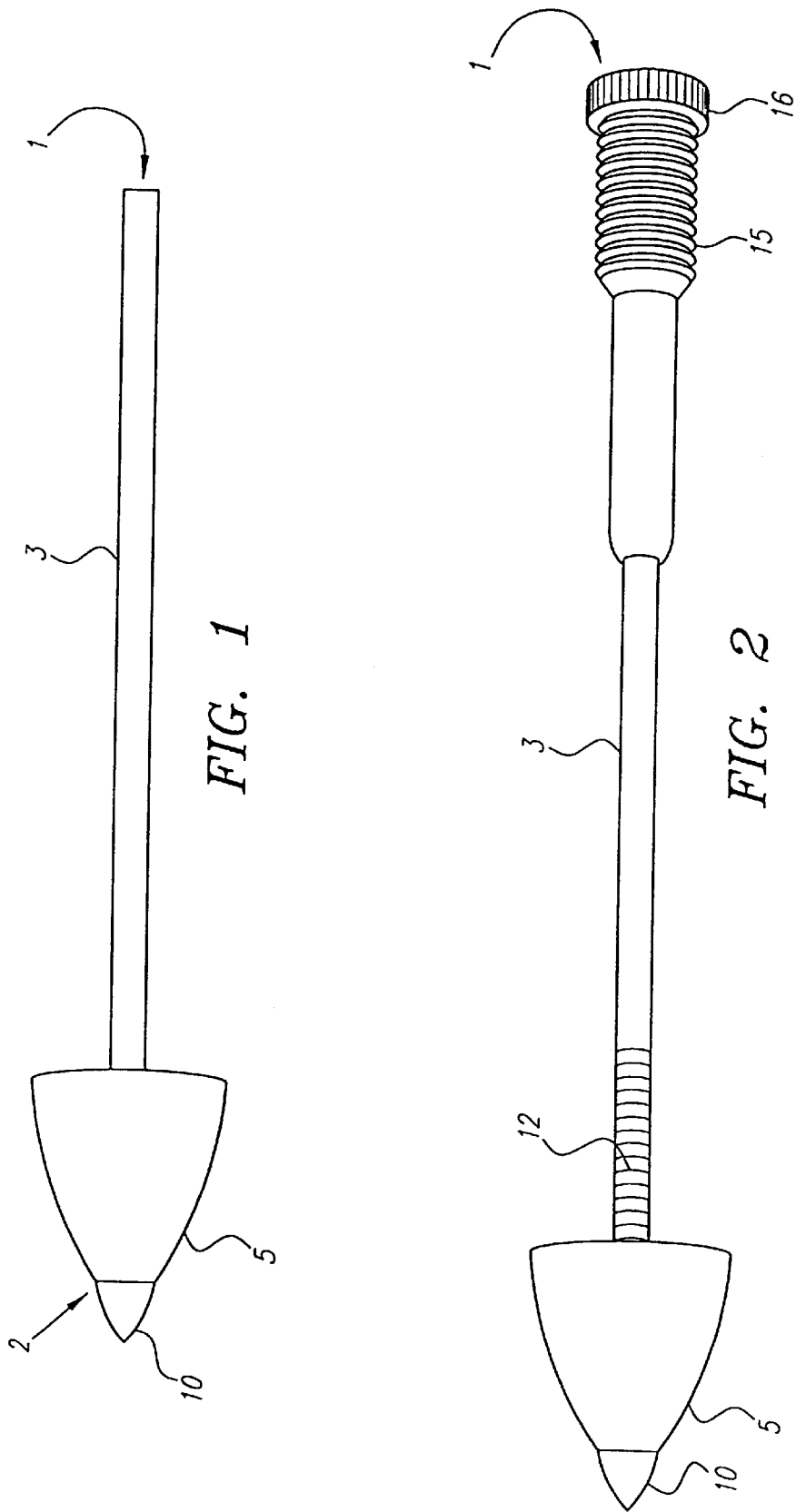

INTRODUCER/DILATOR WITH BALLOON PROTECTION AND METHODS OF USE

This is a continuation of U.S. application Ser. No. 09/547,953, filed Apr. 12, 2000, now U.S. Pat. No. 6,569,182, which is a continuation of U.S. application Ser. No. 09/149,981, filed Sep. 9, 1998, now U.S. Pat. No. 6,093,173, all of which are expressly incorporated herein by reference in their entirety.

FIELD OF THE INVENTION

The present invention relates generally to an introducer system having dilatation capabilities to facilitate insertion of a medical device into a body tissue, including a patient's vascular system. More particularly, the introducer protects the medical device from damage and the body tissue from trauma during insertion.

BACKGROUND OF THE INVENTION

Catheters or cannulas with relatively large diameters are commonly used in various surgical procedures, which include draining fluid from a body cavity, delivering fluid to a body tissue, and introducing surgical and diagnostic tools. To access a body tissue for insertion of these large catheters or cannulas, a guidewire is traditionally used, as described by Seldinger in *Br. J.* 2(6026):21–22 (1976), incorporated herein by reference in its entirety. For example, to insert an internal jugular cannula to provide venous drainage for cardiopulmonary bypass during coronary artery bypass grafting surgery, a patient's right internal jugular vein is first punctured by a small diameter needle. A guidewire is then inserted through the needle into the internal jugular vein. The needle is withdrawn, leaving the guidewire in the blood vessel. A dilator is inserted over the guidewire into the puncture site to enlarge the opening into the internal jugular vein. The dilator is removed and the venous drainage cannula is inserted over the guidewire into the internal jugular vein. After final placement of the cannula, the guidewire is removed, leaving the cannula in the internal jugular vein and available to drain venous blood to a cardiopulmonary bypass machine. In this approach, dilators are used to enlarge an opening on the body tissue for inserting cannulas, and therefore, often traumatize the body tissue.

To reduce the trauma associated with these access devices, thin wall construction using elastomeric materials has been attempted. However, access devices formed of these materials possess a tendency to buckle or bulge during insertion. To overcome the problem of buckling and folding, an adjustable vascular introducer formed of a rolled up plastic sheath in tube form surrounded by a coaxial elastic sheath was described in *Cardiovasc. Intervent. Radiol.* 2:169–171 (1989), incorporated herein by reference in its entirety. This device would expand around the oversized portion of a balloon catheter as it passed through the device. This adjustable introducer, however, has an expandable circular cross-section which limits its applicability beyond balloon valvuloplasty.

Other introduction devices which utilize a trocar or dilator inside a straight or curved cannula to facilitate insertion of the cannula have been described in Klyce et al., U.S. Pat. No. 4,863,430, incorporated herein by reference. Although these devices simplify the steps for inserting a cannula, they lack the ability to protect the cannula, especially when mounted with fragile, exposed, external balloons, from damage during insertion.

A need therefore exists for an introducer system which provides dilation capabilities to facilitate insertion of a medical device into a body tissue, and provides protection for the device and the body tissue from trauma during insertion.

SUMMARY OF THE INVENTION

The present invention provides an introducer system having the ability to dilate an incision on a body tissue for insertion of a medical device, said introducer further having the ability to protect the medical devices and body tissue from injury during insertion. The introducer system comprises an elongate shaft having a proximal and a distal end. A flexible sleeve is mounted on the distal end of the shaft. When the shaft is positioned within a lumen of a cannula, having a proximal end, a distal end, and a lumen therebetween, the sleeve is adapted to circumferentially cover the outer surface of the distal end of the cannula. The flexible sleeve, which is typically also expandable, may be constructed using elastomeric or lubricious material. The elongate shaft may be made of flexible material, e.g. plastic. In certain embodiments, the shaft may include a coil which also provides flexibility for the shaft.

In an alternative embodiment, the proximal end of the shaft may have a collet and a screw lock proximal to the collet adapted for securing the introducer in the lumen of a cannula. The screw and collet also provide a hemostatic seal for the cannula. The distal end of the elongate shaft may include an angulated tip which enlarges an opening into a body tissue, thereby facilitating insertion of a cannula.

The present invention also provides methods for introducing a cannula into a body tissue, including a patient's blood vessel. The methods employ an introducer insertable within a lumen of the cannula, said introducer having a proximal and distal end, and a flexible sleeve mounted on the distal end of the shaft and adapted to cover a distal end of the cannula. After an incision is made on the body tissue, the distal end of the cannula is inserted through the incision into the body tissue with the sleeve covering the outer surface of the distal end of the cannula. This feature is particularly significant in a cannula having an expandable balloon mounted at its distal end in that the balloon is protected from being punctured by the sometimes—calcific plaque of a vessel wall. After final placement of the cannula, the elongate shaft is retracted, whereby the sleeve is inverted and drawn into the lumen of the cannula, thereby removing the sleeve from the outer surface of the distal end of the cannula. The shaft and sleeve are subsequently withdrawn from the lumen of the cannula.

It will be understood that there are many advantages to using an introducer/dilator with balloon protection as disclosed herein. For example, the introducer of the present invention provides (1) dilatation capability, thereby obviating the need for another dilator, (2) a flexible shaft which can be easily accommodated in any curved or straight cannula, (3) protection for a body tissue from trauma during insertion, (4) protection for a medical device from being damaged during insertion, (5) a shaft and sleeve which are easily removed after final placement of the medical device, and (6) a restraint on the outer diameter of the medical device which helps to minimize the cross-sectional profile of the device for insertion into a vessel or other body tissue.

BRIEF DESCRIPTION OF THE DRAWINGS

FIG. 1 depicts a preferred embodiment of an introducer/dilator with balloon protection.

FIG. 2 depicts an alternative preferred embodiment of an introducer/dilator with balloon protection.

DETAILED DESCRIPTION OF THE PREFERRED EMBODIMENTS

Figure 3:
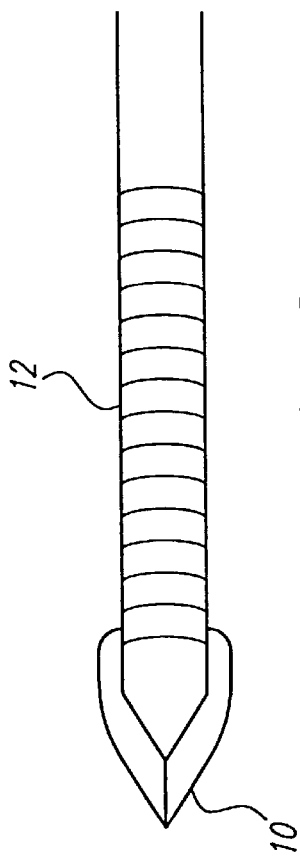
FIG. 3 depicts a distal end of an introducer/dilator without balloon protection.

The devices and methods disclosed herein facilitate insertion of various medical devices, including infusion catheters, aspirators, balloon occluders, pressure monitors, and arterial or venous catheters. A preferred embodiment of an introducer/dilator with balloon protection according to the invention is illustrated in FIG. 1. The introducer/dilator has proximal end 1, distal end 2, and elongate shaft 3. Distal end 2 further comprises tip 10 adapted for insertion into a body tissue. Flexible sleeve 5 is mounted proximal to tip 10 for protecting a medical device.

An alternative embodiment of the introducer/dilator with balloon protection is illustrated in FIG. 2. In this embodiment, elongate shaft 3 further comprises a coil 12 to provide flexibility. Proximal end 1 has collet 15 and screw lock 16 adapted to securely engage a proximal end of a medical device, thereby locking the introducer securely within a lumen of the medical device.

Figure 4:
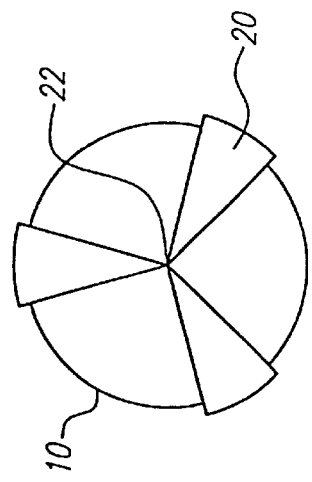
FIG. 4 depicts an end view of the tip depicted in FIG. 3.

FIG. 3 depicts a distal end of an introducer/dilator without balloon protection. In this embodiment, tip 10 is constructed using a plurality of geometric shapes. This is further illustrated in FIG. 4 which depicts an end view of the tip having three prisms 20, each extending distally and sharing a common point 22 at a vertex. Construction of the tip utilizing other numbers of different geometric cuts is also possible to facilitate insertion and dilation in a body tissue.

The length of the elongate shaft is generally between 3 and 15 inches, preferably approximately 7 inches. The diameter of the elongate shaft is generally between 0.05 and 0.25 inches, preferably approximately 0.127 inches. The length of coil from the distal end of the elongate shaft is generally between 2 and 5 inches, preferably approximately 3.5 inches. The foregoing ranges are set forth solely for the purpose of illustrating typical device dimensions. The actual dimensions of a device constructed according to the principles of the present invention may obviously vary outside of the listed ranges without departing from those basic principles.

Figure 5:
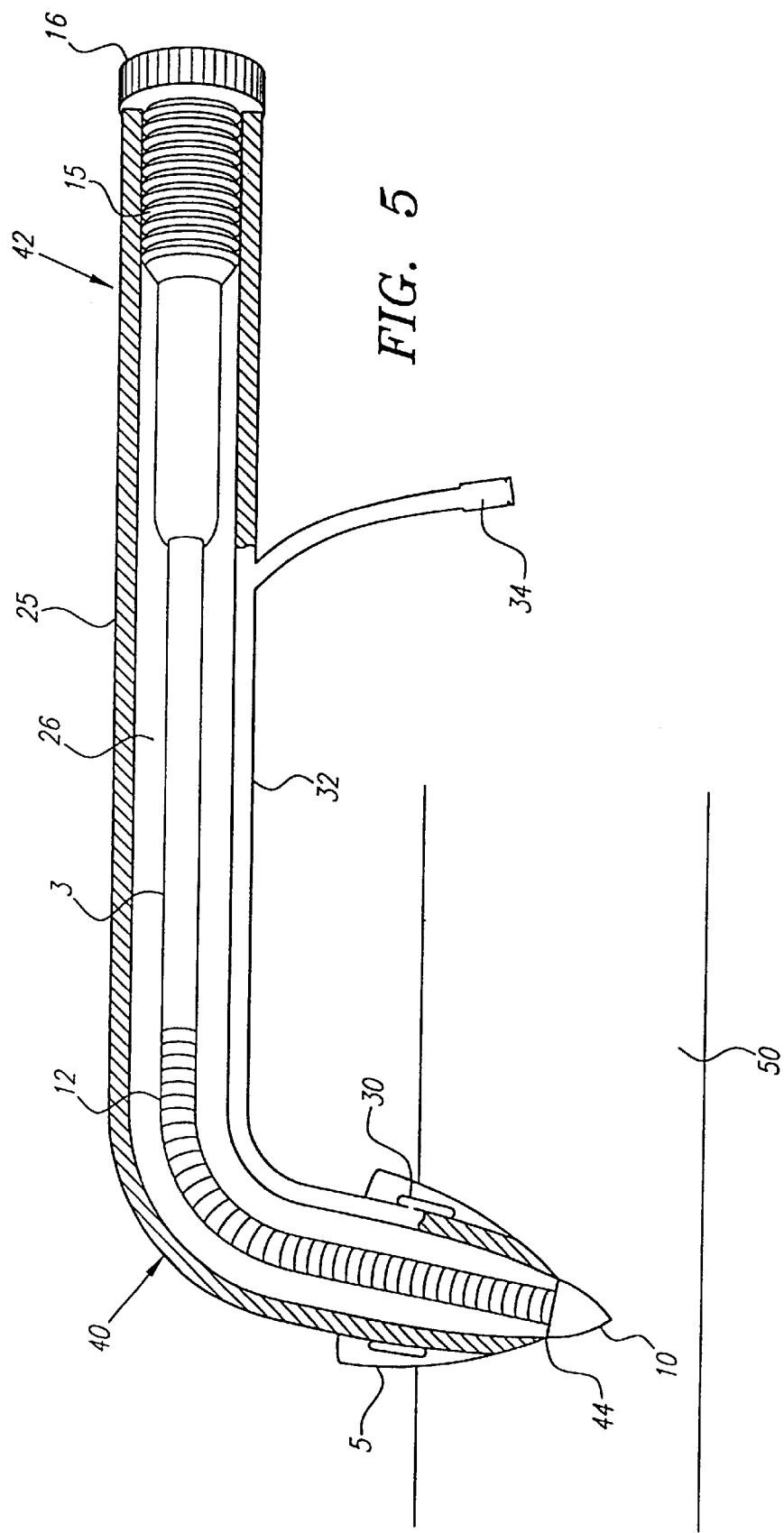
FIG. 5 depicts an introducer/dilator with balloon protection positioned within a lumen of a cannula entering an aorta.
Figure 6:
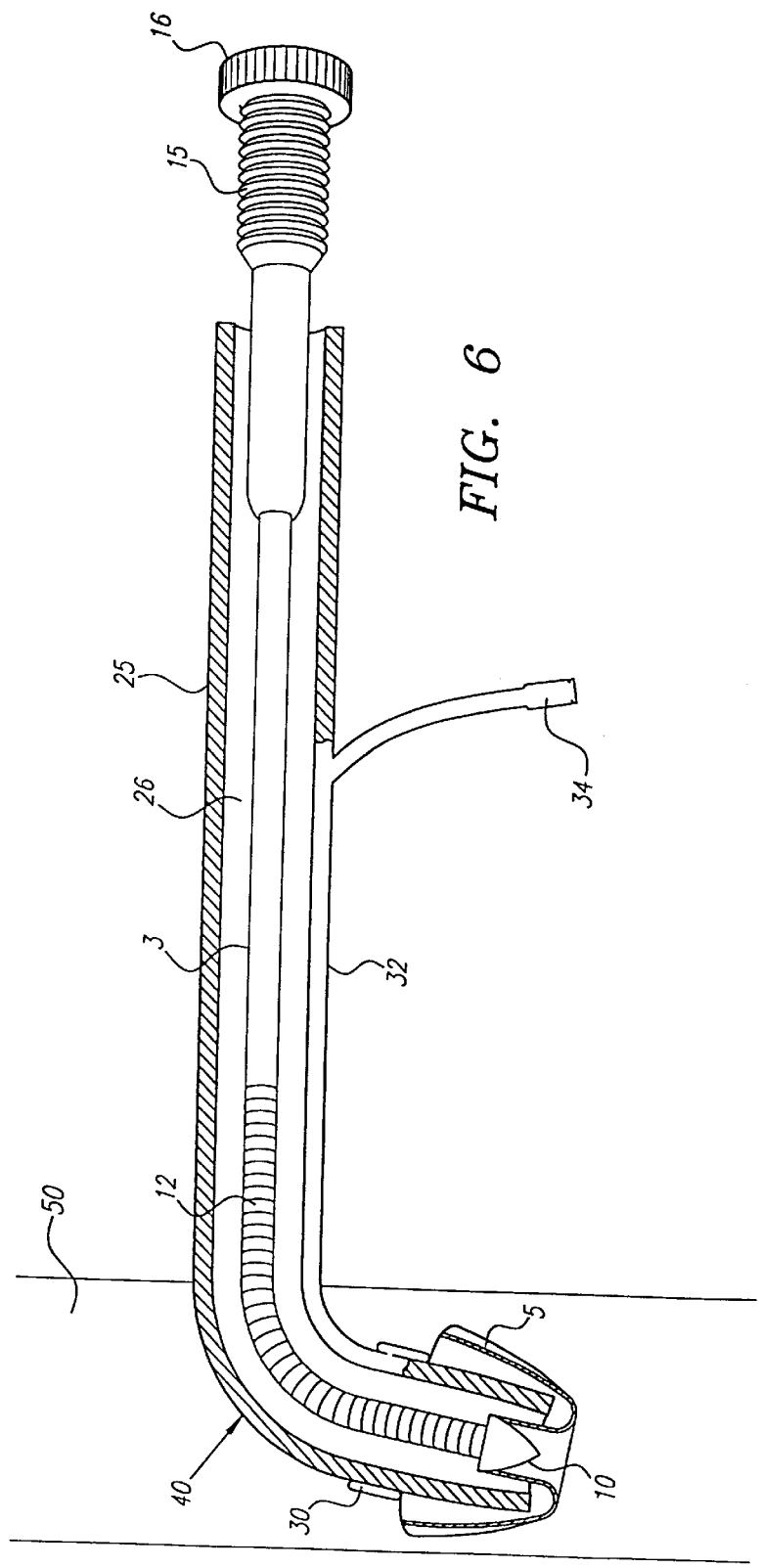
FIG. 6 depicts withdrawal of the introducer/dilator with balloon protection as depicted in FIG. 5.

Methods of using the invention are illustrated in FIGS. 5 and 6. FIG. 5 depicts an introducer/dilator with balloon protection positioned within a lumen of a cannula entering an aorta. During cardiopulmonary bypass, cannula 25 having expandable balloon 30 mounted at distal end 40 is inserted into a patient's ascending aorta 50 to provide circulatory isolation of the heart and coronary blood vessels from the peripheral vascular system. The cannula has lumen 26 for delivering oxygenated blood from the bypass oxygenator machine 55 to the aorta. Expandable balloon 30 is in communication with inflation lumen 32 and inflation port 34. Distal region 40 of the cannula is angled in relation to proximal region 42. Elongate shaft 3 is also angled within the cannula lumen at coil 12. Tip 10 protrudes from distal opening 44 of the cannula. A collet 15 and screw lock 16 secure the introducer/dilator at the proximal region of the cannula.

Figure 7:
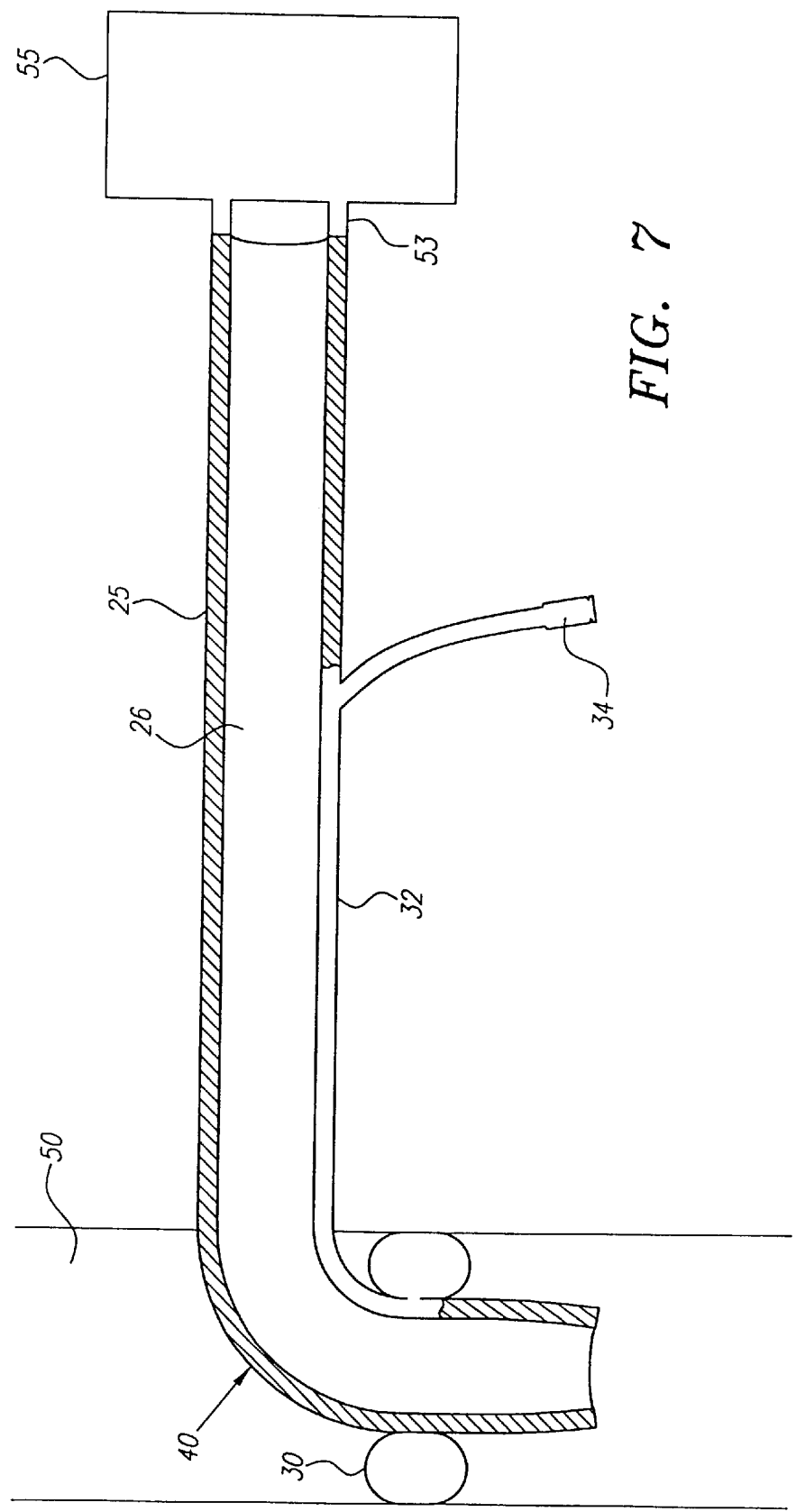
FIG. 7 depicts the cannula of FIG. 6 connected to a bypass-oxygenator machine.

When in use, the cannula 25 containing the introducer/dilator with balloon protection is introduced through an incision made on the aorta 50. Tip 10 facilitates entry of the cannula by enlarging the incision on the aorta, thereby functioning as a dilator. As distal region 40 of the cannula enters the incision, flexible sleeve 5 protects the distal end of the cannula and expandable balloon 30 from damage by the sometimes—calcific aortic plaque. The flexible sleeve also protects the aorta from blunt trauma during insertion of the cannula. After the cannula is positioned within the aorta, screw lock 16 is disengaged at the proximal region of the cannula so that shaft 3 and sleeve 5 can be withdrawn proximally. As the shaft is withdrawn into the lumen of the cannula, flexible sleeve 5 is inverted, thereby releasing the balloon as shown in FIG. 6. As shown in FIG. 7, after the shaft and sleeve are completely removed from the lumen of the cannula, the balloon can be inflated through inflation lumen 32 and inflation port 34 to occlude the aorta, thereby providing isolation of the heart and coronary blood vessels from the peripheral vascular system. Cardiopulmonary bypass can then be initiated by delivering oxygenated blood from a bypass-oxygenator machine 55 to the aorta (shown in FIG. 7). The bypass-oxygenator machine 55 can be connected to the cannula 25 through fitting 53.

Figure 8:
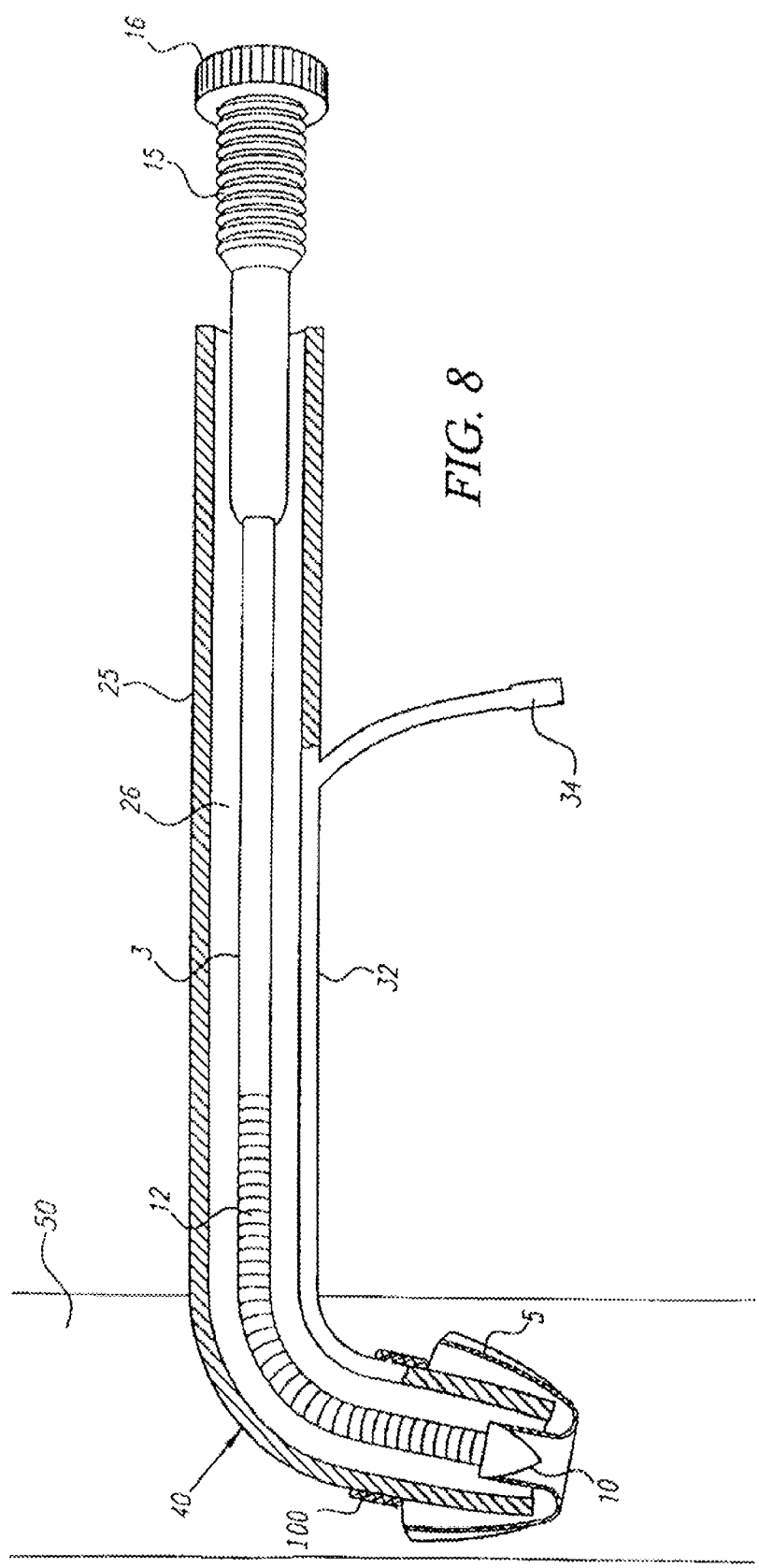
FIG. 8 depicts withdrawal of the introducer/dilator with filter protection.

In addition to the aortic cannula described above, the devices and methods disclosed herein can be utilized in inserting other medical devices into blood vessels or organs, such as atherectomy devices, angioplasty catheters, coronary sinus catheters, percutaneous gastrostomy tubes, intra-aortic balloons, suprapubic catheters, and aortic cannulas with filter 100 as disclosed in Barbut et al., U.S. Pat. No. 5,769,816, incorporated herein by reference in its entirety. FIG. 8 shows the present invention in use with such a filter.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A cannula introducer system, comprising:
   a cannula having a proximal end, a distal end, and a lumen therebetween;
   an elongate shaft having proximal and distal ends, said shaft insertable through the lumen of the cannula;
   a flexible sleeve mounted on the distal end of the shaft, wherein the sleeve is adapted to circumferentially cover the distal end of the cannula when the shaft is positioned within the lumen of the cannula; and
   a filter operable from the distal end of the cannula.

2. The cannula introducer system of claim 1, wherein the proximal end of the cannula is adapted to receive oxygenated blood from a bypass-oxygenator machine.

3. The cannula introducer system of claim 1, wherein the flexible sleeve is an elastomeric sleeve.

4. The cannula introducer system of claim 1, wherein the sleeve comprises a lubricious material.

5. The cannula introducer system of claim 1, wherein the elongate shaft is flexible.

6. The cannula introducer system of claim 1, wherein the elongate shaft further comprises a coil.

7. The cannula introducer system of claim 1, further comprising a collet at the proximal end of the elongate shaft.

8. The cannula introducer system of claim 1, further comprising an angulated tip adapted for insertion into a body tissue at the distal end of the elongate shaft.

9. The cannula introducer system of claim 1, wherein the filter is expandable.

10. The cannula introducer system of claim 1, wherein the filter comprises a mesh material.

11. The cannula introducer system of claim 1, wherein the sleeve circumferentially covers the filter.

12. The cannula introducer system of claim 1, wherein the filter is mounted on the distal end of the cannula.

13. A method for protecting a patient from embolization during an open or minimally invasive surgical procedure, comprising:

inserting a distal end of a cannula into the aorta, the cannula having a lumen, an expandable filter mounted at the distal end, and a flexible sleeve covering the filter;

removing the sleeve from the expandable filter through the lumen of the cannula; and expanding the filter to capture embolic material in the aorta.

14. The method of claim 13, wherein the distal end of the cannula is inserted into the aorta through an incision.

15. The method of claim 13, wherein the sleeve is mounted on a distal end of an elongate shaft inserted through a lumen of the cannula.

16. The method of claim 13, wherein the sleeve comprises a lubricious material.

17. The method of claim 13, wherein the cannula connects to a bypass-oxygenator machine.

18. The method of claim 13, further comprising the step of delivering blood and cardioplegia solution through the cannula.

19. The method of claim 13, further comprising the step of performing coronary artery bypass grafting surgery.

* * * * *